United States Patent [19]

Tymchuck

[11] Patent Number: 5,976,084
[45] Date of Patent: Nov. 2, 1999

[54] STANDARDIZED TEST FOR DYSPHAGIA

[75] Inventor: Donald L. Tymchuck, Minnetonka, Minn.

[73] Assignee: Regents of the University of Minnesota, Minneapolis, Minn.

[21] Appl. No.: 08/957,050

[22] Filed: Oct. 24, 1997

[51] Int. Cl.$^6$ ..................................................... A61B 5/00
[52] U.S. Cl. ........................ 600/300; 128/898; 424/9.1; 600/407
[58] Field of Search .................................. 600/300, 407, 600/410, 425, 437; 128/898; 424/9.1, 9.41, 9.411

[56] References Cited

PUBLICATIONS

Bisch, E.M., et al., "Pharyngeal Effects of Bolus Volume, Viscosity, and Temperature in Patients with Dysphagia resulting from Neurologic Impairment and in Normal Subjects", *J. of Speech and Hearing Research*, 37, 1041–1049, (1994).

Chen, M.Y., et al., "Clinical and Videofluroscopic Evaluation of Swallowing in 41 patients with Neurologic Disease", *Gastrointest. Radiol.*, 17, 95–98, (1992).

Coster, S.T., et al., "Rheology and the Swallow–Safe Bolus", *Dysphagia*, 1, 113–118, (1987).

Crary, M.A., et al., "Clinical Influences of Volume and Viscosity in Neurogenic Dysphagia", *Poster Presentation at the American Speech–Language and Hearing Assn. Convention, New Orleans*, 1–13, (1994).

Dantas, R.O., et al., "Effect of Swallowed Bolus Variable on Oral and Pharyngeal Phases of Swallowing", *Am. Physiological Soc.*, 258, G675–G681, (1990).

Hamlet, S., et al., "Normal Adult Swallowing of Liquid and Viscous Material: Scintigraphic Data on Bolus Transit and Oropharyngeal Residues", *Dysphagia*, 11, 41–47, (1996).

Kim, C.H., et al., "Effect of Viscosity on Oropharyngeal and Esophageal Emptying in Man", *Digestive Diseases and Sciences*, 39, 1, 189–192, (1994).

Ku, D.N., et al., "A Kinematic Study of the Oropharyngeal Swallowing of a Liquid", *Annals of Biomedical Engineering*, 18, 665–669, (1990).

Li, M., et al., "Viscosity Measurements of Barium Sulfate Mixtures for Use in Motility Studies of the Pharynx and Esophagus", *Dysphagia*, 7, 17–30, (1992).

Mann, L.L., et al., "Development of an objective method for assessing viscosity of formulated foods and beverages for the dysphagic diet", *J. of the Am. Dietetic Assn.*, 96, 6, 585–588, (1996).

Martin, A.W., et al., "Dietary Management of Swallowing Disorders", *Dysphagia*, 6, 129–134, (1991).

Martin, B.J., et al., "The Association of Swallowing Dysfunction and Aspiration Pneumonia", *Dysphagia*, 9, 1–6, (1994).

Miller, J.L., et al., "The Influence of Bolus Volume and Viscosity on Anterior Lingual Force During the Oral Stage of Swallowing", *Dysphagia*, 11, 117–124, (1996).

Pardoe, E.M., "Development of a Multistage Diet for Dysphagia", *J. of the Am. Dietetic Assn.*, 93, 5, 568–571, (1993).

Reimbers–Neils, L., et al., "Viscosity Effects on EMG Activity in Normal Swallow", *Dysphagia*, 9, 101–106, (1994).

Robertson, H.M., et al., "A Strategy for Providing Food to the Patient with Neurologically Based Dysphagia", *J. of Can. Dietetic Assn*, 54, 4, 198–201, (1993).

Shoemaker, A., "Objective Measure of Liquid Viscosity in Dysphagia Care", *Advances in Speech and Language*, 15–17, (1996).

Stanek, K., et al., "Factors Affecting use of Food and commerical agents to thicken liquids for indiviiduals with swallowing disorders", *J. of the American Dietetic Assn.*, 92, 4, 488–490, (1992).

Womack, P., et al., "Solving the Mystery of Dysphagia", *Dietary Manager*, 4–7, (1992).

Zenner, P.M., et al., "Using Cervical Auscultation in the Clinical Dysphagia Examination in Long–Term Care", *Dysphagia*, 10, 27–31, (1995).

Felt, P., "Nutritional Management of Oropharyngeal Dysphagia for the Adult Patient: A Therapist's Guide," First Four Chapters of Spiral–Bound Book plus references, pp. 1–13.

*Primary Examiner*—John P. Leubecker
*Assistant Examiner*—Bryan K. Yarnell
*Attorney, Agent, or Firm*—Schwegman, Lundberg, Woessner & Kluth, P.A.

[57] ABSTRACT

Dysphagia, or difficulty in swallowing, can cause choking, aspiration of food or liquid into the lungs, incomplete administration of medication, and discomfort to the victims. A method is provided for evaluating the severity of Dysphagia. The method comprises providing at least two sets of orally ingestible materials, each set of orally ingestible material comprising at least two compositions of like materials differing significantly in one property selected from the group consisting of viscosity, adhesiveness, cohesiveness and yield force. A patient ingests a first one of the at least two compositions from a first set of the at least two sets, examining the patients for a dysphagic response to the ingestion of the first one of the at least two compositions, and noting any dysphagic responses. Steps b), c) and d) are repeated for another set of orally ingestible materials which another set of the at least two sets of orally ingestible materials characterizes a property that is different from a property selected from the group consisting of viscosity, adhesiveness, cohesiveness and yield force characterized by the first one of the at least two compositions from a first set of the at least two sets of orally ingestible material.

23 Claims, No Drawings

5,976,084

STANDARDIZED TEST FOR DYSPHAGIA

BACKGROUND OF THE INVENTION

1. Field of the Invention

Dysphagia is a condition or symptom defined as a difficulty in swallowing. The present invention relates to a method for the standardized measurement of the quality or degree of dysphagia and a kit used for that method.

2. Background of the Art

Dysphagia, or difficulty in swallowing, is a condition or symptom which can be caused by many different conditions, injuries or diseases. Dysphagia can cause choking, aspiration of food or liquid into the lungs, incomplete administration of medication, and discomfort to the victims. These factors can at least discomfort a patient, but may also interfere with or complicate conventional treatment of patients. Among the many contributions to or causes of dysphagia are head injuries, Parkinsonism, Alzheimer's disease, muscular dystrophy, cerebral palsy, cancer, medication side effects, advanced HIV infections, gastrointestinal disorders, and brain tumors. It has been estimated that more than 10,000 patients a year choke to death as a result of dysphagia.

Dysphagia is a well-recognized condition and has been studied and addressed by doctors and nutritionists (Robertson, Helen M. And Pattillo, Margaret S., *Journal of the Canadian Dietetic Association*, Vol. 54, No. 4, Winter 1993). Such studies have noted that the condition is affected by the temperature, pH, viscosity, volume, size and shape of particulate matter in the ingested sample, and that these conditions can affect the likelihood of a bolus passing safely through the swallowing process.

Robertson et al. (supra) formulated test substances for the videofluoroscopy examination of the patient for visual examination of dysphagia effects on individual patients. An actual structural evaluation of the patient's dysphagia was observed under fluoroscopy. It was further noted in the preparation of the blended materials used during the fluoroscopic examination that the foods used were not by nature smooth and homogeneous, and that they may vary in cohesiveness, adhesiveness, viscosity and texture. It was noted that where materials exhibited the worst two-phase characteristics (fibrous materials in a liquid), the materials were further blended with whipped potato to produce smoother, more cohesive products. Various test points based upon viscosity (ranging from dry, crumbly material, 2000 cps, 800 cps, 250 cps and 100 cps) and texture (Dysphagia/Dental soft, Minced/chopped, and Puree') are intended to be identified on the food preparation menus offered to patients.

Felt, Pat and Anderson, Coleen, *Nutritional Management of Oropharyngeal Dysphagia for the Adult Patient*: A Therapist's Guide, 1990 describes the diagnosis and treatment of dysphagia, diets for dysphagia sufferers, and related matters. The publication noted that swallowing, and therefore dysphagia, occurs in three phases: the oral, pharyngeal and esophageal phases. The publication identifies and provides guidelines for the three phases, and identifies properties of the food or bolus which can attribute to the problem or relieve the problem. Amongst the properties are viscosity, elasticity, and particulateness. Diets based on nutritional requirements and physical properties are provided.

Womak, Pam and Pope, Jane Erwin, *Solving the Mystery of Dysphagia*, Dietary Manager," March 1992 describes the swallowing process and provides guidelines for the temporary diet management of the dysphagia patient. The viscosity and texture of the food as part of the rheologic evaluation of the food, as well as the seasoning and temperature, are emphasized.

Li, Brasseur, Kern and Dodds, Dysphagia, 7:17–30, 1992 made detailed viscosity measurements on barium sulfate mixtures for use in motility studies of the pharynx and esophagus. The mixtures also used flavorings. The viscosity of the mixtures was described with respect to the concentration of ingredients so that a standard viscosity could be provided for use in motility studies. Viscosity was the primary rheologic property considered for standardization, although viscosity was considered as a function of shear rate. The conclusion suggests that a test kit of bolus substances in which other rheologic characteristics (e.g., elasticity) are included would be of great clinical value.

Although treatment and diagnosis of dysphagia have been addressed, there is little standardization within the medical profession for evaluation of the condition, except by extreme methods such as fluoroscopic examination. In view of dramatic cost controls applied to medical treatment, such evaluations and diagnostic procedures would not likely be approved.

BRIEF DESCRIPTION OF THE INVENTION

A method and kit for use in the measurement of the severity of dysphagia are provided by a kit containing samples of materials to be swallowed by a patient, the samples having standardized properties of various parameters, including at least some of viscosity, cohesiveness, adhesiveness, brittleness, lubricity, particularity (particulateness) and yield force of the bolus. The samples are to be swallowed by the patient, with the parameters varying from sample to sample, and the effects of the samples, as indicated by the ability or comfort level of the patient in swallowing the samples are recorded for each of the parameters. The specific severity of the dysphagia (and/or a profile of the dysphagia) can be evaluated and identified for each specific patient based upon the level of each parameter with which a patient is comfortable, and by charting of the responses to each and every one of the parameters, a more clinical valuation of the specific degree (and possibly even type) of dysphagia problem can be identified and used in a more precise evaluation of appropriate forms of foods for dietary nourishment. A kit may be provided with groups of samples of materials which vary most predominantly with respect to a single parameter, with different groups available for each of the parameters. Volumetric doses may be premeasured or a measuring cup provided. A chart or conversion table/reference table may also be provided.

DETAILED DESCRIPTION OF THE INVENTION

A method for measuring the severity of dysphagia is performed by providing samples of materials to be swallowed by a patient, each sample being characterized by controlled parameters, at least some of the parameters being selected from viscosity, adhesiveness, cohesiveness, brittleness, particulateness, lubricity and yield force of the bolus. Samples are swallowed by the patient, and the samples are administered with variations identified with respect to each of the parameters being considered in the evaluation/diagnosis. Various degrees of swallowing difficulty may be identified with respect to a progression of value change in the parameter, with the option of the clinician being to stop the progression when a degree of dysphagia has been encountered by the patient during the testing. That is, for example, when the adhesiveness of the bolus is progressing in a scholastic fashion from 1 (lowest adhesiveness to the palate or pharyngeal area), through 2, 3, 4 and/or 5 (for example), if clear difficulty is observed by the clinician at a level of 3, the test may be stopped so as not to endanger the patient. The data indicating a clear problem at level 3 would be sufficient data to provide a meaningful evaluation of the severity of the condition, in combination with data from other parameter testing efforts.

The ultimate goals for the Development of a Diagnostic and Nourishment System for People with Swallowing Difficulties are:
1) To determine the textural properties of foods that are relevant to people with swallowing disorders.
2) To quantify those textural properties by instrumental and sensory techniques.
3) To develop a set of samples, Diagnostic Kit, that can be used to assess the range of textures relevant to patients with swallowing disorders.
4) To develop a line of food with textures related to those of the Diagnostic Kit that can be purchased by hospitals and/or patients.

A method of for providing a standard measure of dysphagia according to the present invention may comprise the steps of:
a) providing at least two sets of orally ingestible materials, each set of orally ingestible material comprising at least two compositions of like materials differing in one property selected from the group consisting of viscosity, adhesiveness, cohesiveness and yield force,
b) having a patient ingest a first one of said at least two compositions from a first set of said at least two sets of orally ingestible material,
c) non-fluoroscopically examining the patients for a dysphagic response to the ingestion of the first one of said at least two compositions, and
d) noting any dysphagic responses, then repeating steps b), c) and d) for another set of said at least two sets of orally ingestible materials which another set of said at least two sets of orally ingestible materials characterizes a property selected from the group consisting of viscosity, adhesiveness, cohesiveness and yield force which is different from a property selected from the group consisting of viscosity, adhesiveness, cohesiveness and yield force characterized by said first one of said at least two compositions from a first set of said at least two sets of orally ingestible material. It is desirable to confine the variation of the property to be tested within each group of samples as much as possible to a single property variable (e.g., by varying only the lubricity without varying the particularity). However, variations in one physical property almost invariably causes alterations in at least one other property. It is therefore a target in the practice of this invention to keep the variations within individual sets (e.g., the particulateness set) focussed upon the variation of that single property. The other properties which could be considered in other sets of materials used to evaluate dysphagia could be minimized and should display less significant variations in those incidental or secondary (as opposed to the primary property being evaluated) properties. There is no precise way of mathematically describing the tolerable range of variations in secondary properties, but the variations tend to take care of themselves by standardization of the test materials. Similarly, when a substantial variation in properties is discussed, this means that the variations as between samples are enough so that a statistically meaningful variation in properties is provided. For example, with respect to viscosity, a variation as between 1000 and 1001 mPas would not be significant. Substantial in this sense means that the differences, over significant numbers of tests, would be expected to display some variation in responses in test patients.

The invention also describes methods for the preparation of liquid and semi-solid samples in the prototype Diagnostic Kit which will be used by speech pathologists to assess the range of textural attributes that are thought to be relevant to patients with swallowing disorders. These textural attributes include at least some of the following: Viscosity, Yield Force, Cohesiveness, Brittleness, Lubricity, Particulateness and Adhesiveness.

At least two preferably at least three, and more preferably at least four separate parameters selected from viscosity, adhesiveness, cohesiveness and yield force of the bolus are used in the identification and evaluation of the severity of the dysphagia. A matrix of the results of evaluation with respect to each of the parameters may be prepared and a specific profile of dysphagia or a category or level of dysphagia (as defined in supplemental materials provided with a testing kit) may be defined. By defining a specific profile, level or category of dysphagia, a diet may be prescribed to address the specific needs of the patient. By using this non-invasive, non-fluoroscopic examination, lower cost technical personnel (e.g., medical assistants versus medical doctors) may perform the test, lower cost equipment and materials may be used, and the tests have been shown by actual clinical tests to compare favorably with the results obtained by the considerably more expensive testing procedures.

The samples may be provided in a number of manners, including, but not limited to the following fashions. Actual premade samples of ingestible materials may be provided in containers. Each container may have the appropriate amount for a single or multiple dose. There would be individual containers for each variation in the property to be evaluated. For example, with regard to a standardized scholastic measurement of adhesiveness, there would be containers with materials having at least an adhesiveness of 1 and 2, preferably 1, 2 and 3, and more preferably at least 1, 2, 3 and 4. For the last option, there would be four separate containers or vials with an individual dose (or multiple doses in case of failure of the first dosing because of physical error as opposed to dysphagic response). This determination of a value for the property (selected from a significant range of values) provides a high level of assurance of the values for each of the test materials, and therefore a more consistent and assured basis for accurate comparison of results. The only factors which would be likely to cause variations probably would be expiration of storage dates of the samples, exposure of the samples to the environment for a sufficiently long period to cause changes in the properties (e.g., by evaporation or deterioration of materials), variations in manufacture of the individual samples kit-to-kit, or the like.

Dry compositions to be mixed with specific amounts of water may be provided for each of the parameters and even for each of the variations within each of the parameters. By providing dry materials, the volume of the kit can be reduced, as water does not have to be included with the test materials, but may be added by the clinician. This introduces a possibility for some greater variation in results due to likely variations in the amounts of liquid added, incomplete dispersion/dissolution of materials in the water, failure to measure or transfer the actually intended volumes, and other variations introduced by handling of the materials. Similarly, concentrates of the individual samples or an intermediate which may be diluted to each of the variations used to evaluate a single parameter may be provided. This is an intermediate choice between completely formulated and completely dry supply of the testing ingredients. As noted, a single material (dry or concentrated) may be provided for each parameter to be investigated or measured, and the single material (the base composition) may be diluted by specified amounts of liquid (e.g., water) to provide the individual test sample. For example, 25 grams of a base composition may be mixed with 5, 10, 15 and 17.5 milliliters of water lo provide the specific testing compositions for use in the standardization method of the dysphagia for the patient.

The materials used for the testing compositions must of course be ingestible and should not cause distress to the patient, and should be inert with respect to aspects or properties which in themselves could independently effect dysphagia beyond the properties under consideration. For example, materials should be checked for specific allergic reactions with a particular patient, highly sensitizing foods (strong spices or herbs) should be avoided (unless a specific component of the test is designed to evaluate that dysphagia response), peppers, astringents, alcohol, coagulants, allergens and the like are types of materials to be avoided unless they are specifically part of the intended design response of the evaluation program. The materials to be used in standardizing the various parameters within the evaluation/testing compositions should be selected on a combined basis of non-toxicity, low allergic effects, and palatability. If the last is not considered, pre-contact responses (e.g., gagging from aroma or vapors) may alter the physiological/rheologic responses which are intended to be evaluated. Coloration may be added to the materials, and this in fact can provide a very useful function. As the coloration from a standard or base composition would be less intense (less optical density) as it was diluted, the inclusion of a color in the materials when they are mixed or before they are mixed would assist in providing a visual identification of the strength of the property being evaluated. For example if a green dye were present in the base composition, as more water/volume of base composition was added, the density of the green coloration would decrease. It would be less likely for a clinician to then misread the relative value of the measured property since simple visual comparison could confirm the relative strength of the property. Dye coloration may also be useful for assisting in the visual examination of the passage of the material (as with a dark blue coloration used when endoscopically viewing passage of the bolus (e.g., with the scope inserted through the nasal passage or through the throat).

A kit according to the present invention might include at least three separate compositions (dry, concentrated or fully formulated) which are formulated or could be reformulated into more than one subformulations, each of the subformulations being representative of a specific value of a parameter selected from the group consisting essentially of viscosity, adhesiveness, cohesiveness and yield force of the bolus, each subformulation differing from the other subformulation with respect to one of those parameters by a predetermined amount. Preferably there would be at least two subformulations for each parameter, more preferably at least three or at least four subformulations available for each parameter. The more preferred construction of a kit provides preformulated samples which do not have to be diluted, each parameter having at least two and preferably at least three separate premade formulations representing differing values of the parameters. The still more preferred construction provides multiple differentiated premade samples of at least the four identified parameters. The samples are preferably supported in closed containers within supports within the kit, particularly supports which provide nesting sites such as provided for beverages in carrying containers, where the containers are supported in three dimensions against movement.

A grid, matrix, table or graph is preferably provided for entry of the data from the tests performed on patients. The grid, matrix, table or graph is preferably color coded in different sections to visually assist in the identification of the severity of the dysphagia indicated by the test. Position within the grid, matrix, table or graph may be based upon multiple axes, quadrants, etc. so that the combination of values indicates a condition. A lookup table may also be provided so that a cumulative reading of the data is indicative of a specific type of dysphagia. This can be done in a number of ways. For example, a specific result on a specific test may be provided with an arbitrary, but designed value. The specific results from each of the tests may be combined into a resultant value. This resultant value may be examined in the lookup table to provide a specific dysphagia profile or categorization of dysphagia. Alternatively, the specific combinations of separate values may be listed in reference tables so that each specific combination of different values (e.g., 2 for viscosity, 3 for adhesiveness, 2 for cohesiveness and 4 for yield force) would be looked for in the tables to identify a specific profile for dysphagia or specific type of dysphagic response (description or test profile) to the test. The diet would be chosen based upon this standardized identification of the type of dysphagia.

Also described herein are some of the instrumental techniques used to quantify the textural attributes of the samples in the prototype Diagnostic Kit.

Viscosity

The prototype Diagnostic Kit contains three Viscosity levels (with 4, 5, 6, 7, etc. being possible). Each level was formulated with and without barium sulfate, which is an insoluble radiopaque material which provides positive contrast for x-ray procedures. The material may also be provided without blue dye where visual inspection of the bolus is not essential.

Sample Preparation

The following ingredients were used in the preparation of the Viscosity levels:

a. Granulated Sucrose: Crystal Sugar®, United Sugars Corporation; Moorhead, Minn.

b. Fine grain citric acid: Lot DCC4035. Cargill, Corn Milling Division; Eddyville, Iowa.

c. Lemon flavor: Unsweetened soft drink mix, Kool-Aid®. Kraft General Foods Inc.; White Plains, N.Y.

d. Sodium benzoate: Lot MAOB4143. Haarman & Reimer Corp., Food Ingredients Division; Elkhart, Ind.

e. Potassium sorbate: Sorbistat-K®, Lot 609091-S6121, Pfizer Inc., Chemical Division; New York, N.Y.

f. Modified waxy maize corn starch: MIRA-SPERSE® 623, Lot TL0240-2A. A. E. Staley Manufacturing Company; Decatur, Ill.

g. Bottled drinking water: Kandiyohi Bottled Water Company; Willmar, Minn.

h. Barium sulfate: E-Z-PAQUE®, E-Z-EM Inc.; Westbury, N.Y.

i. Blue color: FD&C Blue No. 1. Chr. Hansen's Laboratory Inc.; Milwaukee, Wis.

The Viscosity levels were prepared according to the following procedure:

1. For each level, the required amounts (Table 1) of sucrose, water, lemon flavor, citric acid, potassium sorbate and sodium benzoate, and blue color or barium sulfate were weighed (scale model P1210; The Mettler Instrument Corporation, Hightstown, N.J.) in a 250-ml mixing jar (Sunbeam-Oster, Household Products; Schaumburg, Ill.).

2. The ingredients were mixed at low speed for 2 minutes using an electric mixer (8 speed Osterizer blender.

Sunbeam-Oster, Household Products). The corresponding amount of modified starch was then added (Table 1) and additional mixing was done at low speed for 2 minutes using the electric mixer.

3. After mixing, the sample was placed in a 1-L filtering flask with side arm (Fisher Scientific Co.; Pittsburgh, Pa.) and vacuum applied for 5 minutes using an Airejector™ water aspirator (Fisher Scientific Co.).
4. The vacuumed sample was then placed in 60-mL plastic bottles (Fisher Scientific Co.) and kept in hot water (electric stove, General Electric Company; Chicago, Ill.) for 45 minutes @ 75–80° C. and then placed for 45 minutes in a refrigerator @ approximately 5° C. (General Electric Company).
5. Samples were kept at refrigerated temperature (~5° C.) until one hour before being analyzed.

2.2 Instrumental Measurement of Viscosity

Measurements of shear stress and shear rate were done at 25° C. using a rotational viscometer (model RV 2, Haake; Paramus, N.J.) and concentric cylinder geometry (models NV and MVIIP). Samples were placed in the viscometer and left undisturbed for 15 minutes at 25° C. before measurements.

Shear stress was measured by increasing the shear rate between 700–1400 l/s (Viscosity level I) and 1–150 l/s (Viscosity levels II and III) in a stepwise mode. Viscosity levels II and III showed non-Newtonian behavior; therefore, the apparent viscosity among samples was compared at a constant shear rate of 50 l/s (Wood, 1968).

Viscosity was also evaluated by a back extrusion technique (Osorio and Steffe, 1987) using the TZ.XT2® Texture Analyzer (Texture Technologies Corporation; Scarsdale, N.Y.). An acrylic probe with a diameter of 1.5 in. and a height of 0.75 in. and a cup with a diameter of 2 in. were used. From the sample's surface, the probe was lowered 8 mm at a speed of 10 mm/s and the maximum force during penetration was measured.

2.3 Results

Viscosity level I showed Newtonian behavior and at 50 l/s the apparent viscosity was between 1.4–2.0 mPa.s. Viscosity levels II and III showed pseudoplastic behavior and could be modeled by power law equations. Viscosity levels II and III had apparent viscosities of approximately 240 and 840 mPa.s at 50 l/s (that is, at seconds to the negative first power, the inverse of the seconds, at $s^{-1}$) (Table 2).

Stress relaxation measurements indicated that none of the Viscosity level samples showed perceptible yield stress values.

3.0 Yield Force

The prototype Diagnostic Kit contains three Yield Force levels. As before, each level was formulated with and without barium sulfate.

3.1 Sample Preparation

Instead of modified waxy maize corn starch, xanthan gum Lot 5737 (Continental Colloids Inc.; West Chicago, Ill. Phone (708) 231–8650) was the thickener used for the preparation of the Yield Force levels. Sucrose, citric acid, lemon flavor, sodium benzoate, potassium sorbate, bottled drinking water, and optionally barium sulfate or blue color were also used.

The Yield Force levels were prepared according to the following procedure:
1. For each level, the required amounts (Table 4) of sucrose, water, lemon flavor, citric acid, potassium sorbate and sodium benzoate, and blue color or barium sulfate were weighed (scale model P1210; The Mettler Instrument Corp.) in a 250-ml mixing jar (Sunbeam-Oster, Household Products).
2. The ingredients were mixed at low speed for 2 minutes using an electric mixer (8 speed Osterizer blender. Sunbeam-Oster, Household Products). The corresponding amount of xanthan gum (Table 4) was then added and additional mixing was done for 5 minutes using the electric mixer.
3. After mixing, the sample was placed in a 1-L filtering flask with side arm (Fisher Scientific Co.) and vacuum applied for 5 minutes using an Airejector™ water aspirator (Fisher Scientific Co.).
4. The sample was then placed in 60-mL ointment jars (Fisher Scientific Co.) and kept in hot water (electric stove, General Electric Company) for 45 minutes @ 75–80° C. and then placed for 45 minutes in a refrigerator @ approximately 5° C. (General Electric Company).
5. Samples were kept at refrigerated temperature (~5° C.) until analyzed.

3.2 Instrumental Measurement of Yield Force

The force associated to the yield stress was measured using the TA.XT2® Texture Analyzer (Texture Technologies Corporation; Scarsdale, N.Y.) and a back extrusion technique (Osorio and Steffe, 1987). An acrylic probe with a diameter of 1.5 in diameter and a height of 0.75 in. and a cup with a diameter of 2 in. were used.

This instrumental method allows for the simultaneous measurement of Firmness, Yield Force and Adhesiveness. From the sample's surface, the probe was lowered 8 mm at a speed of 1 mm/s and the maximum force during penetration was defined as Firmness. The probe was held at this depth for 3 minutes and the equilibrium force was defined as Yield Force. After this period of time the probe was withdrawn from the sample and the maximum negative force was defined as Adhesiveness.

3.3 Results

All samples showed pseudoplastic flow behavior with a yield stress. The Apparent viscosities (@ 50 l/s) of the Yield Force levels were approximately 200 mPa.s (level I), 1000 mPa.s (level II) and 2900 mPa.s (level III) (Table 5).

Table 6 shows the values of Yield Force for levels I, II and III.

Cohesiveness

The prototype Diagnostic Kit contains two Cohesiveness levels. As before, each level was formulated with and without barium sulfate.

4.1 Sample Preparation

Apple sauce (Prestige™ Fancy Apple Sauce; Kraft Food Service Inc.; Glenview, Ill.), xanthan gum, citric acid, sodium benzoate, and potassium sorbate, and barium sulfate or blue color were used to prepare the Cohesiveness levels.

The Cohesiveness levels were prepared according to the following procedure:
1. For each level, the required amounts (Table 7) of citric acid, sodium benzoate and potassium sorbate, and barium sulfate or blue color were weighed (scale model P1210; The Mettler Instrument Corp.) in a 250-ml mixing jar (Sunbeam-Oster, Household Products).
2. The ingredients were mixed at low speed for 2 minutes using an electric mixer (8 speed Osterizer blender. Sunbeam-Oster, Household Products). The corresponding amount of xanthan gum (Table 7) was then added, and additional mixing was done for 3 minutes using the electric mixer.
3. After mixing, the sample was placed in a 1-L filtering flask with side arm (Fisher Scientific Co.) and vacuum applied for 5 minutes using an Airejector™ water aspirator (Fisher Scientific Co.).
4. The sample was then placed in 60-mL ointment jars (Fisher Scientific Co.) and kept in hot water (electric stove, General Electric Company) for 45 minutes @ 75–80° C. and then placed for 45 minutes in a refrigerator @ approximately 5° C. (General Electric Company).

5. Samples were kept at refrigerated temperature (~5° C.) until analyzed.

4.2 Instrumental measurements of cohesiveness The TA.XT2® Texture Analyzer (Texture Technologies Corporation; Scarsdale, N.Y.) was used in a simple uniaxial compression mode (Bourne, 1982) to evaluate the Cohesiveness levels. An aluminum plate with a diameter of 36 mm and a gap of 5 mm were used.

Approximately 1 tablespoon of sample was placed on the Texture Analyzer platform, compressed to a gap of 5 mm, and the excess of sample cleaned. The sample was held for 10 minutes to allow for temperature stabilization and relaxation of stresses.

The sample was then compressed to 10% strain (0.5 mm) at a speed of 1 mm/s and allowed to relax for 3 minutes while the relaxation force was being measured.

4.3 Results

The samples showed stress relaxation typical of viscoelastic materials with the stress falling to En equilibrium value higher than zero. The stress relaxation of the Cohesiveness levels could be described by a Generalized Maxwell model.

The Initial and Equilibrium forces of the Cohesiveness levels are shown in Table 8.

Adhesiveness

The prototype Diagnostic Kit contains two different Adhesiveness levels. As before, each level was formulated with and without barium sulfate.

5.1 Sample preparation

The following ingredients were used to prepare the Adhesiveness levels:

a. Skippy® creamy peanut butter. Best Foods Division, CPC International Inc.; Inglewood Cliffs, N.J.

b. Crisco® all-vegetable shortening. Procter & Gamble; Cincinnati, Ohio.

c. Mazola® corn oil. Best Foods Division, CPC International Inc.; Inglewood Cliffs, N.J.

d. Blue color: FD&C Blue No. 1 lake. Chr. Ilansen's Laboratory Inc.; Milwaukee, Wis. Phone (414) 476–3630.

The Adhesiveness levels were prepared according to the following procedure:

1. For each Adhesiveness level, the required amounts (Table 9) of peanut butter, vegetable shortening and vegetable oil, and barium sulfate or blue color were weighed (scale model P1210; The Mettler Instrument Corp.) in a 250-ml mixing jar (Sunbeam-Oster, Household Products).

2. The ingredients were heated for 1 minute in a microwave oven (model R-9470; Sharp Electronics Corporation; Mahwah, N.J.) at the high level setting and then mixed for 1 minute at low speed in the electric mixer.

3. The sample was then placed in 60-mL ointment jars (Fisher Scientific Co.) and then placed for 45 minutes in a refrigerator @ approximately 5° C. (General Electric Company).

4. Samples were kept at room temperature (20–25° C.) until analyzed.

5.2 Instrumental measurements of Adhesiveness

The TA.XT2® Texture Analyzer (Texture Technologies Corporation; Scarsdale, N.Y. and a back extrusion technique were used to measure Adhesiveness. This instrument method allows for the simultaneous measurement of Firmness, Yield Force and adhesiveness was described previously.

Table 10 shows values of Adhesiveness for levels I and II.

Conclusions

The prototype Diagnostic Kit consists of 10 samples with the following texture attributes and levels:

Viscosity: levels I, II and III

Yield Force: levels I, II and III

Cohesiveness: levels I and II

Adhesiveness: levels I and II

The TA.XT2® Texture Analyzer (Texture Technologies Corporation; Scarsdale, N.Y.) is the preferred equipment for the instrumental measurement of the relevant texture attributes. It can be used for the instrumental evaluation of Viscosity, Yield Force, Cohesiveness and Adhesiveness.

The Haake rotational viscometer (Haake; Paramus, N.J.) and other similar equipments, i.e., Brookfield viscometer, can be used only for the instrumental evaluation of Viscosity and Yield Force.

TABLE 1

Ingredients used in the Viscosity levels.

| Ingredient | Level I (grams) | | Level II (grams) | | Level III (grams) | |
|---|---|---|---|---|---|---|
| | non-Barium | +Barium | non-Barium | +Barium | non-Barium | +Barium |
| Sucrose | 21.60 | 21.60 | 100.00 | 100.00 | 100.00 | 100.00 |
| Water | 176.80 | 176.80 | 97.80 | 97.80 | 97.80 | 97.80 |
| Lemon flavor | 1.00 | 1.00 | 1.00 | 1.00 | 1.00 | 1.00 |
| Citric acid | 0.40 | 0.40 | 0.40 | 0.40 | 0.40 | 0.40 |
| Potassium sorbate | 0.10 | 0.10 | 0.10 | 0.10 | 0.10 | 0.10 |
| Sodium benzoate | 0.10 | 0.10 | 0.10 | 0.10 | 0.10 | 0.10 |
| Subtotal | 200.00 | 200.00 | 200.00 | 200.00 | 200.00 | 200.00 |
| Blue color | 0.02 | 0.00 | 0.02 | 0.00 | 0.02 | 0.00 |
| Barium sulfate | 0.00 | 20.00 | 0.00 | 20.00 | 0.00 | 20.00 |
| Subtotal | 200.02 | 220.00 | 200.02 | 220.00 | 200.02 | 220.00 |
| Modified starch | 0.00 | 0.00 | 5.00 | 4.00 | 6.70 | 6.20 |
| Total | 200.02 | 220.00 | 205.02 | 224.00 | 206.72 | 226.20 |

TABLE 2

Apparent viscosities (@ 50 1/s) of the Viscosity levels.

| Viscosity Level | non-Barium (mPa.s) | +Barium (mPa.s) |
|---|---|---|
| I | 1.4 | 2.0 |
| II | 239 | 239 |
| III | 859 | 830 |

TABLE 3

Maximum forces during back extrusion of the Viscosity levels.

| Viscosity Level | non-Barium (Newtons) | +Barium (Newtons) |
|---|---|---|
| I | 0.32 | 0.308 |
| II | 0.424 | 0.432 |
| III | 0.531 | 0.528 |

TABLE 4

Ingredients used in the Yield Force levels.

| Ingredient | Level I (grams) | | Level II (grams) | | Level III (grams) | |
|---|---|---|---|---|---|---|
| | non-Barium | +Barium | non-Barium | +Barium | non-Barium | +Barium |
| Sucrose | 21.60 | 21.60 | 21.60 | 21.60 | 21.60 | 21.60 |
| Water | 176.80 | 176.80 | 176.80 | 176.80 | 176.80 | 176.80 |
| Lemon flavor | 1.00 | 1.00 | 1.00 | 1.00 | 1.00 | 1.00 |
| Citric acid | 0.40 | 0.40 | 0.40 | 0.40 | 0.40 | 0.40 |
| Potassium sorbate | 0.10 | 0.10 | 0.10 | 0.10 | 0.10 | 0.10 |
| Sodium benzoate | 0.10 | 0.10 | 0.10 | 0.10 | 0.10 | 0.10 |
| Subtotal | 200.00 | 200.00 | 200.00 | 200.00 | 200.00 | 200.00 |
| Blue color | 0.02 | 0.00 | 0.02 | 0.00 | 0.02 | 0.00 |
| Barium sulfate | 0.00 | 20.00 | 0.00 | 20.00 | 0.00 | 20.00 |
| Subtotal | 200.02 | 220.00 | 200.02 | 220.00 | 200.02 | 220.00 |
| Xanthan gum | 1.16 | 1.16 | 3.00 | 3.00 | 8.20 | 8.20 |
| Total | 201.18 | 221.16 | 203.02 | 223.00 | 208.22 | 228.20 |

TABLE 5

Apparent viscosities (@ 50 1/s) of the Yield Force levels.

| Yield Force Level | non-Barium (mPa.s) | +Barium (mPa.s) |
|---|---|---|
| I | 197 | 184 |
| II | 965 | 935 |
| III | 2901 | 2942 |

TABLE 6

Equilibrium forces during back extrusion of the Yield Force levels.

| Yield Force Level | non-Barium (mPa.s) | +Barium (mPa.s) |
|---|---|---|
| I | 0.270 | 0.240 |
| II | 0.341 | 0.362 |
| III | 0.730 | 0.692 |

TABLE 7

Ingredients used in the Cohesiveness levels.

| Ingredient | Level I (grams) | | Level II (grams) | |
|---|---|---|---|---|
| | Non-Barium | +Barium | non-Barium | +Barium |
| Applesauce | 198.60 | 198.60 | 198.60 | 198.60 |
| Citric acid | 1.00 | 1.00 | 2.00 | 1.00 |
| Potassium sorbate | 0.20 | 0.20 | 0.20 | 0.20 |
| Sodium benzoate | 0.20 | 0.20 | 0.20 | 0.20 |
| Subtotal | 200.00 | 200.00 | 200.00 | 200.00 |
| Blue color | 0.02 | 0.00 | 0.02 | 0.00 |
| Barium sulfate | 0.00 | 20.00 | 0.00 | 20.00 |
| Subtotal | 200.02 | 220.00 | 200.02 | 220.00 |
| Xanthan gum | 5.00 | 5.00 | 14.00 | 14.00 |
| Total | 205.02 | 225.00 | 214.02 | 234.00 |

TABLE 8

Initial and equilibrium forces of the Cohesiveness levels.

| Cohesiveness level | Initial force (Newtons) | | Equilibrium force Newtons) | |
|---|---|---|---|---|
| | non-Barium | +Barium | non-Barium | +Barium |
| I | 0.459 | 0.458 | 0.085 | 0.087 |
| II | 2.243 | 2.267 | 0.470 | 0.486 |

TABLE 9

Ingredients used in the Adhesiveness levels.

| Ingredient | Level I (grams) | | Level II (grams) | |
|---|---|---|---|---|
| | Non-Barium | +Barium | non-Barium | +Barium |
| Peanut butter | 105.00 | 100.00 | 150.00 | 144.40 |
| Vegetable oil | 70.00 | 75.00 | 25.00 | 27.80 |
| Shortening | 25.00 | 25.00 | 25.00 | 27.80 |
| Subtotal | 200.00 | 200.00 | 200.00 | 200.00 |
| Blue color | 0.06 | 0.00 | 0.06 | 0.00 |
| Barium sulfate | 0.00 | 20.00 | 0.00 | 20.00 |
| Total | 200.06 | 220.00 | 200.06 | 220.00 |

TABLE 10

Adhesiveness force of the Adhesiveness levels.

| Adhesiveness Level | non-Barium (Newtons) | +Barium (Newtons) |
|---|---|---|
| I | 1.0 | 1.9 |
| II | 14.5 | 15.1 |

What is claimed:

1. A method for providing a standard measure of dysphagia comprising the steps of:
   a) providing at least two sets of orally ingestible materials, each set of orally ingestible material comprising at least two compositions of like materials differing in one property selected from the group consisting of viscosity, adhesiveness, cohesiveness and yield force,
   b) having a patient ingest a first one of said at least two compositions from a first set of said at least two sets of orally ingestible material,
   c) non-fluoroscopically examining the patients for a dysphagic response to the ingestion of the first one of said at least two compositions, and
   d) noting any dysphagic responses,
then repeating steps b), c) and d) for another set of said at least two sets of orally ingestible materials which another set of said at least two sets of orally ingestible materials characterizes a property selected from the group consisting of viscosity, adhesiveness, cohesiveness and yield force which is different from a property selected from the group consisting of viscosity, adhesiveness, cohesiveness and yield force characterized by said first one of said at least two compositions from a first set of said at least two sets of orally ingestible material.

2. The method of claim 1 wherein at least three sets of orally ingestible materials having at least two compositions are provided, and a first one of said at least two compositions for said third set of orally ingestible material is ingested, repeating steps b), c) and d) for said third set.

3. The method of claim 2 wherein at least four sets of orally ingestible materials having at least two compositions are provided, and a first one of said at least two compositions for said fourth set of orally ingestible material is ingested, repeating steps b), c) and d) for said fourth set.

4. The method of claim 3 wherein each set comprises at least three compositions.

5. The method of claim 4 wherein each composition of each set is fully prepared and identified as to its respective characteristic and is not diluted before ingestion.

6. The method of claim 2 wherein each set comprises at least three compositions.

7. The method of claim 6 wherein each composition of each set is fully prepared and identified as to its respective characteristic and is not diluted before ingestion.

8. The method of claim 6 wherein noting of dysphagic responses from said at least three sets of orally ingestible materials provides information which is used to identify a degree of severity of dysphagia by reference to a separate source of information.

9. The method of claim 2 wherein each composition of each set is fully prepared and identified as to its respective characteristic and is not diluted before ingestion.

10. The method of claim 1 wherein each set comprises at least three compositions.

11. The method of claim 1 wherein each composition of each set is fully prepared and identified as to its respective characteristic and is not diluted before ingestion.

12. The method of claim 1 wherein noting of dysphagic responses provides information which is used to identify a degree of severity of dysphagia.

13. The method of claim 1 wherein values obtained for the results of the tests are provided, and the values obtained for the results of the tests are compared to a table which references an appropriate diet based upon the results of the tests.

14. The method of claim 13 wherein the table is an electronic table.

15. A method for providing a standard measure of dysphagia comprising the steps of
   a) providing at least three sets of orally ingestible materials, each set of orally ingestible material comprising at least two compositions of like materials substantially differing in one property selected from the group consisting of viscosity, adhesiveness, cohesiveness and yield force,
   b) having a patient ingest a first one of said at least two compositions from a first set of said at least three sets of orally ingestible material,
   c) non-invasively examining by imaging means the patients for a dysphagic response to the ingestion of the first one of said at least two compositions, and
   d) noting any dysphagic responses,
then repeating steps b), c) and d) for another set of said at least three sets of orally ingestible materials which another set of said at least three sets of orally ingestible materials characterizes a property selected from the group consisting of viscosity, adhesiveness, cohesiveness and yield force which is different from a property selected from the group consisting of viscosity, adhesiveness, cohesiveness and yield force characterized by said first one of said at least three compositions from a first set of said at least three sets of orally ingestible material.

16. The method of claim 15 wherein said non-invasive means is X-ray fluoroscopy.

17. The method of claim 15 wherein at least three sets of orally ingestible materials having at least two compositions are provided, and a first one of said at least two compositions for said third set of orally ingestible material is ingested, repeating steps b), c) and d) for said third set.

18. The method of claim 15 wherein at least four sets of orally ingestible materials having at least two compositions are provided, and a first one of said at least two compositions for said fourth set of orally ingestible material is ingested, repeating steps b), c) and d) for said fourth set.

19. The method of claim 10 wherein each set comprises at least three compositions.

20. The method of claim 18 wherein each composition of each set is fully prepared and identified as to its respective characteristic and is not diluted before ingestion.

21. The method of claim 20 wherein noting of dysphagic responses from said at least three sets of orally ingestible materials provides information which is used to identify a degree of severity of dysphagia by reference to a separate source of information using an electronic look-up table.

22. The method of claim 15 wherein each set comprises at least three compositions.

23. The method of claim 15 wherein each composition of each set is fully prepared and identified as to its respective characteristic and is not diluted before ingestion.

* * * * *

UNITED STATES PATENT AND TRADEMARK OFFICE
CERTIFICATE OF CORRECTION

PATENT NO.     : 5,976,084
DATED          : November 2, 1999
INVENTOR(S)    : Tymchuck It is certified that error appears in the above-identified patent and that said Letters Patent is hereby corrected as shown below:

On the title page, item [75] should read – Donald L. Tymchuck
                                            Dr. Zata Vickers
                                            Dr. Carlos Aguilar --

Signed and Sealed this

Fifth Day of December, 2000

*Attest:*

Q. TODD DICKINSON

*Attesting Officer*                 *Director of Patents and Trademarks*